United States Patent
deBoisblanc et al.

(10) Patent No.: US 6,454,721 B1
(45) Date of Patent: Sep. 24, 2002

(54) METHOD AND APPARATUS FOR ESTIMATION OF PULMONARY CAPILLARY PRESSURE

(76) Inventors: Bennet P. deBoisblanc, 27 Heron St., New Orleans, LA (US) 70124; Royce W. Johnson, 114 Rimdale, Universal City, TX (US) 78148; Andy Pellett, 1105 Focis St., Metairie, LA (US) 70005; Glenn B. Bell, 3454 Tyler Ct., Ellicott City, MD (US) 21042

(*) Notice: Subject to any disclaimer, the term of this patent is extended or adjusted under 35 U.S.C. 154(b) by 0 days.

(21) Appl. No.: 09/371,327

(22) Filed: Aug. 10, 1999

Related U.S. Application Data

(63) Continuation of application No. PCT/US98/02806, filed on Feb. 11, 1998.
(60) Provisional application No. 60/037,676, filed on Feb. 11, 1997.

(51) Int. Cl.[7] .................................................. A61B 5/00
(52) U.S. Cl. ........................ 600/486; 600/488; 600/561
(58) Field of Search ................................ 600/485, 486, 600/488, 561

(56) References Cited

U.S. PATENT DOCUMENTS

| | | | |
|---|---|---|---|
| 4,869,263 A | 9/1989 | Segal et al. | 128/692 |
| 4,878,898 A | 11/1989 | Griffin et al. | 604/101 |
| 5,048,532 A | 9/1991 | Hickey | 128/675 |

OTHER PUBLICATIONS

PCT International Search Report; PCT International application PCT/US98/02806; May 5, 1998.

PCT International Preliminary Examination Report; PCT International application PCT/US98/02806; Dec. 2, 1998.

*Primary Examiner*—Robert L. Nasser

(57) ABSTRACT

A medical device for triggering the inflation of a pulmonary artery catheter balloon. The device generally comprises a waveform analysis machine that monitors the pulmonary artery blood pressure waveform and triggers the inflation of the catheter balloon at such a time as to cause occlusion of the pulmonary artery during the systolic upstroke. The time of occlusion is then readily apparent in the resulting decaying blood pressure waveform, which may then be used as a basis for compartment model estimation of the pulmonary capillary pressure.

13 Claims, 3 Drawing Sheets

METHOD AND APPARATUS FOR ESTIMATION OF PULMONARY CAPILLARY PRESSURE

RELATED APPLICATIONS

This application is a continuation of PCT international application No. PCT/US98/02806 filed Feb. 11, 1998, which claims priority to U.S. provisional application Serial No. 60/037,676 entitled METHOD AND APPARATUS FOR ESTIMATION OF PULMONARY CAPILLARY AND WEDGE PRESSURES filed Feb. 11, 1997 by the same inventors. By this reference, the full disclosures, including the drawings, of PCT international application No. PCT/US98/02806 and U.S. provisional application Serial No. 60/037,676 are incorporated herein.

FIELD OF THE INVENTION

The present invention relates to cardiopulmonary diagnostics. More specifically, the present invention relates to a data acquisition and timing method and apparatus by which pulmonary capillary pressure may be more readily obtained utilizing known curve fitting techniques such as Gaar's equation.

BACKGROUND OF THE INVENTION

Pulmonary capillary pressure, the blood pressure in the capillaries between the pulmonary artery and the pulmonary vein, is long known as a useful indication of fluid balance in a patient. The measure is particularly useful in patients with sick lungs because the pressure of the blood in the capillaries of the lungs defines the driving force pushing fluid out of the blood and into the air sacs, potentially causing pulmonary edema. Under the current state of the art, pulmonary capillary pressure is obtained by inserting a balloon flotation catheter, such as the well-known Swan-Ganz type flow-directed catheter, through the heart and into a smaller branch of the pulmonary artery. Once the catheter is in place, a balloon at the distal tip of the catheter is inflated to occlude blood flow through the branch. The resulting decaying pressure curve downstream the balloon occlusion is then measured by a data acquisition device, and is thereafter utilized to estimate the pulmonary capillary pressure with well known compartment model formulas such as Gaar's equation.

Unfortunately, the conventional method for obtaining capillary pressure presents significant risk to the patient. Inflation of the catheter's balloon within the pulmonary artery causes a distinct force to be exerted outwardly against the artery's interior wall. A naturally fragile or otherwise weakened artery may not tolerate this outward force, resulting in rupture of the artery. Although not extraordinarily common, the ultimate effect of a ruptured artery is catastrophic to the patient; a surgical team has only between about 30 seconds and three minutes to open the patient's chest and clamp the bleeder before the patient bleeds to death into the plural cavity. To compound the problem, pulmonary artery catheters have a tendency to migrate downstream. As the catheter enters smaller and smaller portions of the arterial branch, the chance for rupture of the artery increases. Because of these inherent risks, it is very important that the measurement not be unnecessarily repeated. Unfortunately, however, clinicians must often repeat the measurement because unless the occlusion takes place during the systolic upstroke it is not readily possible to determine the exact time of occlusion -an important input parameter for the compartment models.

It is therefore a specific object of the present invention to obtain an estimate of the pulmonary capillary pressure without need for unnecessary inflation of a pulmonary artery catheter balloon.

SUMMARY OF THE INVENTION

In accordance with the foregoing objects, the present invention generally comprises a medical device for triggering the inflation of a pulmonary artery catheter balloon. The device generally comprises a waveform analysis machine which monitors the pulmonary artery blood pressure waveform and triggers the inflation of the catheter balloon at such a time as to cause occlusion of the pulmonary artery during the systolic upstroke. The time of occlusion is then readily apparent in the resulting decaying blood pressure waveform, which may then be used as a basis for compartment model estimation of the pulmonary capillary pressure.

Many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Figure 1:
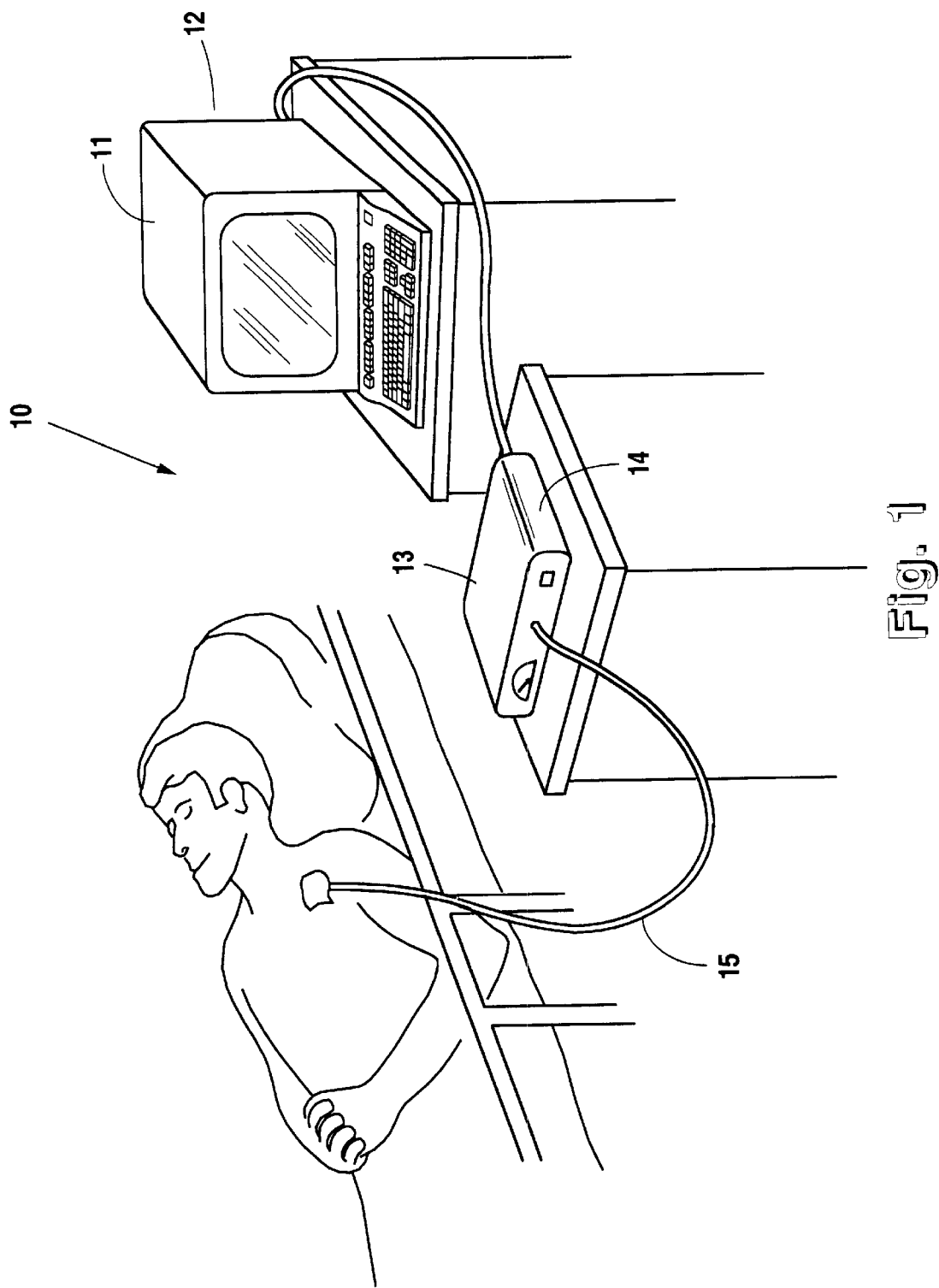
FIG. 1 shows, in perspective overview, the present invention as placed in use with a patient.
Figure 2:
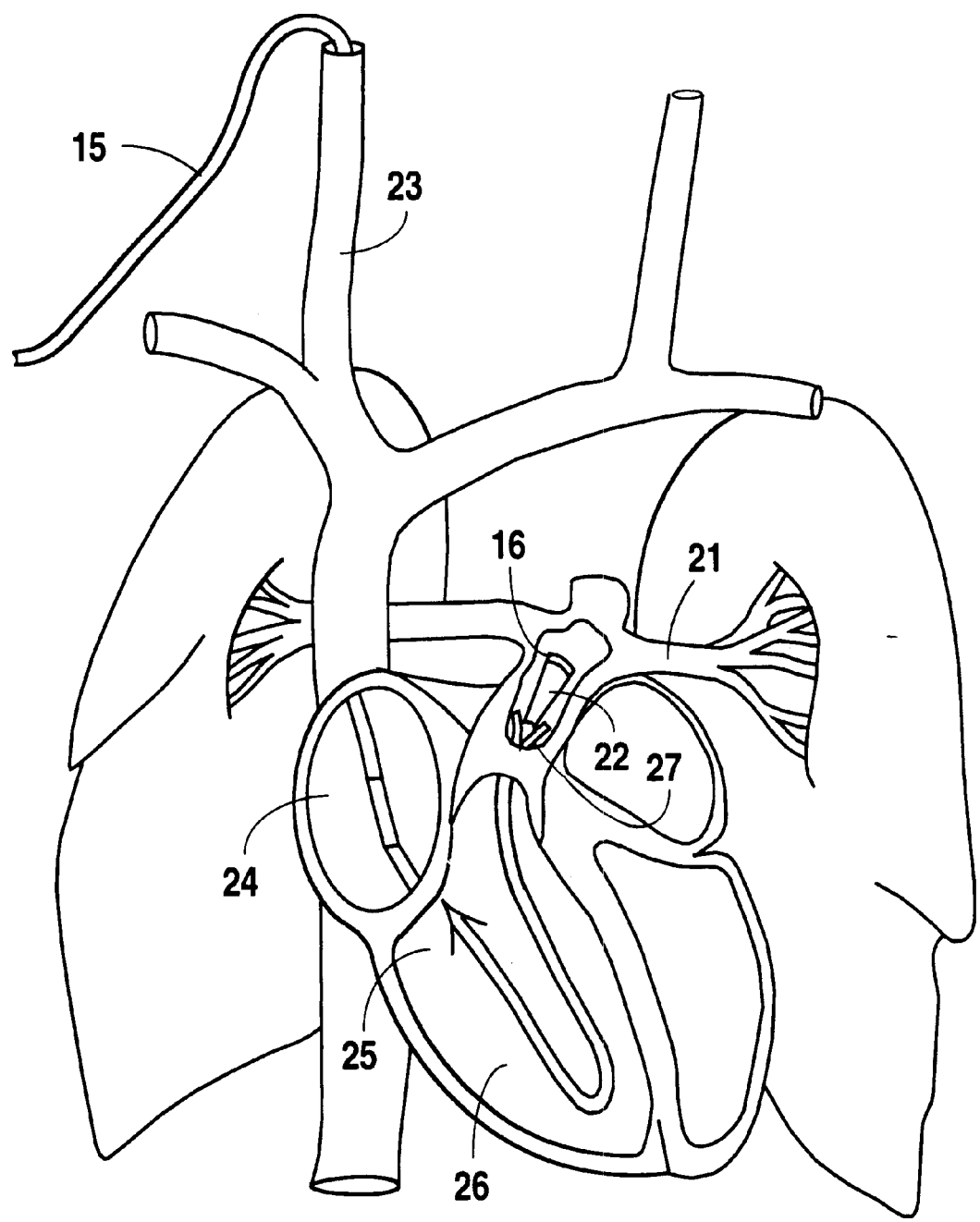
FIG. 2 shows, in cut view, placement of a flow-directed catheter in a human cardiovascular system.
Figure 3:
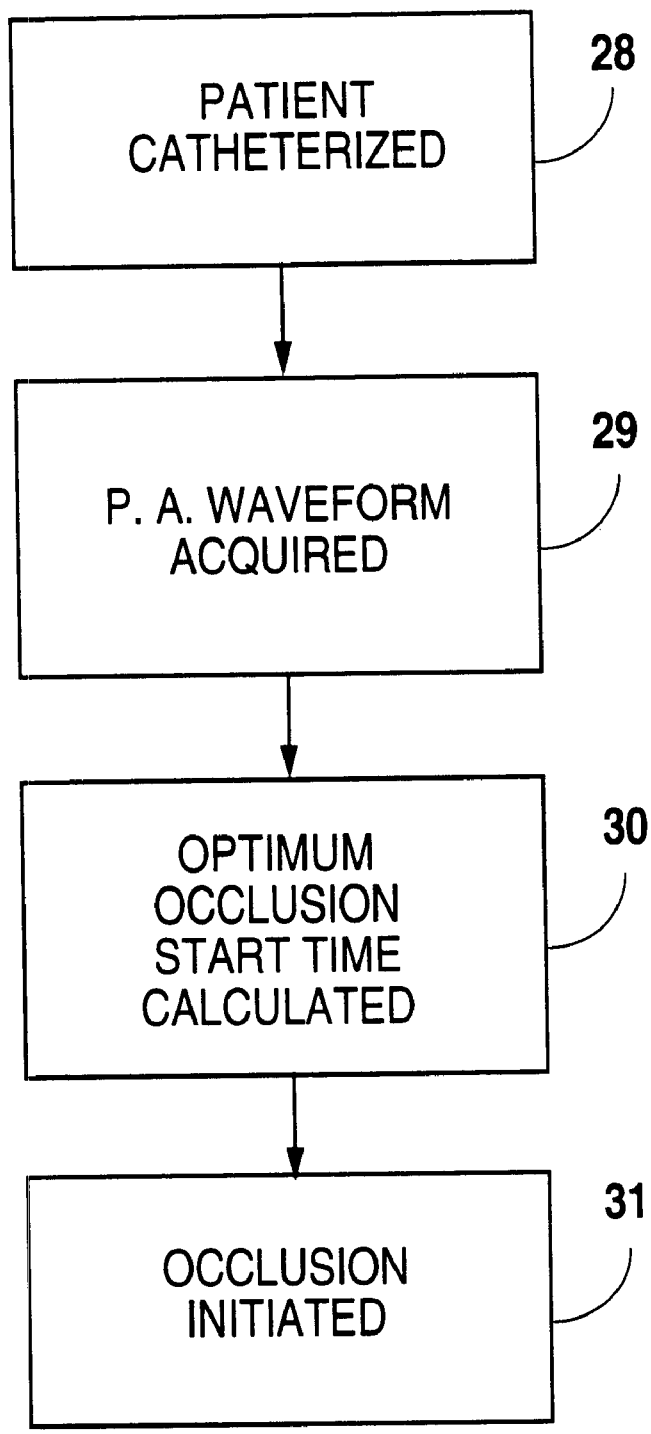
FIG. 3 shows, in flowchart, operation of the implemented invention.

Although those of ordinary skill in the art will readily recognize many alternative embodiments, especially in light of the illustrations provided herein, this detailed description is exemplary of the preferred embodiment of the present invention—a method and apparatus for estimation of pulmonary wedge pressure 10, the scope of which is limited only be the claims appended hereto. In the preferred embodiment, the present invention generally comprises an Apple Macintosh trademark POWERMAC model 8100 with 48 Megabytes internal RAM 11, commercially available from Apple Computers of Cupertino, Calif. and/or its many known distributors; a model NB-AIO-16 12 bit, 16 channel analog to digital data acquisition board 12 under software control of trademark LABVIEW for Macintosh data acquisition software, each commercially available from National Instruments of Austin, Tex. and/or its many known distributors; a syringe pump 14, as is well known in the art for delivering occluding pressure to the balloon of a flow-directed catheter; and a pulmonary artery blood pressure measurement device 13.

The preferred embodiment utilizes a flow-directional catheter 15 equipped at the tip with a stain gauge pressure transducer 16 for measuring the pressure waveform within the pulmonary artery. In implementing the present invention, the catheter 15 is first placed in the patient. As is known to those of ordinary skill in the art, any of a plurality of sites may be chosen for catheterization of the patient.

Specifically, the flow-directed catheter may be inserted in the jugular, subdlavian, femoral or anticubital facies regions. Catheterization in the femoral region presents an increased risk of thrombous formation and catheterization in the subdlavian region presents the remote possibility of puncturing a lung during insertion. Catheterization in the anticubital facies region necessitates immobilization of the patient's arm and impedes utilization of the arm for other purposes such as drug administration. It is therefore preferred that catheterization take place in the jugular region whereby these and other possible complications, such as venospasm, are avoided.

As is known in the art, the chosen insertion point is dissected to the vein which is lifted from the wound by distal and proximal ties. An incision is then made into the vein and held open with a vein holder as the flow-directed catheter is inserted. Assuming insertion through the jugular, the polyurethane balloon 22 is inflated when the tip of the catheter 15 is in the superior vena cava 23. The flow-directed catheter 15 is then guided into the right atrium 24, through the tricuspid valve 25 and into the right ventrical 26. It is important that the polyurethane balloon be soft in order to prevent tachycardia when the tip of the catheter 15 touches the right ventricular wall. Finally, the flow-directed catheter 15 is passed through the pulmonic valve 27 and into the pulmonary artery 21 where it may remain for up to several days. The insertion wound is then dressed; as the flow-directed catheter 15 is almost always used in acutely ill patients, insertion of the catheter 15 and dressing of the wound requires the utmost care and sterile conditions.

Once the patient is catheterized 28 the pulmonary artery blood pressure waveform is acquired 29 by the computer 11. The computer then takes into account any processing delays in the computer 11 and the delay involved in activating the syringe pump 14 to calculate 30 the optimum time to initiate occlusion of the pulmonary artery 21. After the time is determined, and the operator authorizes occlusion, the computer 11 automatically initiates 31 the occlusion. In this manner the occlusion is assured to take place during the systolic upstroke, preventing unnecessary repetition of this hazardous procedure. The post-occlusion waveform is then acquired by the data acquisition board 12 and utilized in the known compartment models.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and the claims drawn hereto. For example, a manual adjustment may be provided to fine-tune the time of occlusion rather than allowing the system to operate under full automation. In any case, because the scope of the present invention is much broader than any particular embodiment, the foregoing detailed description should not be construed as a limitation of the present invention, which is limited only by the claims appended hereto.

What is claimed is:

1. A medical triggering device for use in estimation of pulmonary capillary pressure, comprising:

a pulmonary artery blood pressure transducer;

a waveform analysis machine, in communication with said pulmonary artery blood pressure transducer, said analysis machine being adapted to determine optimum time of occlusion such that occlusion will take place during a systolic upstroke; and a pulmonary occlusion device, in communication with said analysis machine, for occluding the pulmonary artery under the command of the analysis machine.

2. The medical triggering device as recited in claim 1, wherein said pulmonary occlusion device comprises a flow-directional catheter.

3. The medical triggering device as recited in claim 2, wherein said flow-directional catheter comprises a circumferentially inflatable balloon.

4. The medical triggering device as recited in claim 3, wherein:

said inflatable balloon defines a distal portion of said catheter and a proximal portion of said catheter; and said blood pressure transducer comprises a strain gauge pressure transducer in said distal portion of said catheter.

5. A medical triggering device for use in estimation of pulmonary capillary pressure, said medical triggering device comprising:

a pulmonary artery blood pressure transducer; and a waveform analysis machine, in communication with said pulmonary artery blood pressure transducer, said analysis machine being adapted to determine optimum time of occlusion such that occlusion will take place during a systolic upstroke.

6. A method for triggering a pulmonary artery occlusion device, said method comprising the steps of:

placing a catheter into the pulmonary artery of a patient, said catheter comprising pulmonary artery blood pressure transducer;

acquiring a pulmonary blood pressure waveform from said transducer; and processing said waveform to determine optimum time of occlusion such that occlusion will take place during a predeterminable portion of said waveform.

7. The method as recited in claim 6, wherein said processing step comprises accounting for processing delay.

8. The method as recited in claim 6, wherein said processing step comprises accounting for occlusion device delay.

9. The method as recited in claim 6, wherein said catheter further comprises a pulmonary occlusion device.

10. The method as recited in claim 9, further comprising actuating said pulmonary occlusion device based upon the determination of said processing step to effect a desired occlusion.

11. The method as recited in claim 10, wherein said actuating step is in automated response to said waveform.

12. The method as recited in claim 11, wherein said actuating step follows an authorization input.

13. The method as recited in claim 10, further comprising capturing the distal pulmonary artery blood pressure waveform during and after said actuating step.

* * * * *